US011376096B2

(12) United States Patent
Browd et al.

(10) Patent No.: US 11,376,096 B2
(45) Date of Patent: *Jul. 5, 2022

(54) ALIGNING PRE-OPERATIVE SCAN IMAGES TO REAL-TIME OPERATIVE IMAGES FOR A MEDIATED-REALITY VIEW OF A SURGICAL SITE

(71) Applicant: Proprio, Inc., Seattle, WA (US)

(72) Inventors: Samuel R. Browd, Mercer Island, WA (US); James Andrew Youngquist, Seattle, WA (US); Adam Gabriel Jones, Seattle, WA (US)

(73) Assignee: Proprio, Inc., Seattle, WA (US)

( * ) Notice: Subject to any disclaimer, the term of this patent is extended or adjusted under 35 U.S.C. 154(b) by 78 days.

This patent is subject to a terminal disclaimer.

(21) Appl. No.: 16/995,756

(22) Filed: Aug. 17, 2020

(65) Prior Publication Data

US 2020/0375689 A1     Dec. 3, 2020

Related U.S. Application Data

(63) Continuation of application No. 16/749,963, filed on Jan. 22, 2020, now Pat. No. 10,912,625.
(Continued)

(51) Int. Cl.
*G06T 7/73* (2017.01)
*A61B 90/00* (2016.01)
(Continued)

(52) U.S. Cl.
CPC ............. *A61B 90/37* (2016.02); *A61B 90/39* (2016.02); *G06T 7/33* (2017.01); *G06T 7/73* (2017.01);
(Continued)

(58) Field of Classification Search
CPC ........... A61B 90/37; A61B 90/39; G06T 7/33; G06T 7/73; G06T 19/20
See application file for complete search history.

(56) References Cited

U.S. PATENT DOCUMENTS 6,990,220 B2 *  1/2006  Ellis ..................... G16H 50/50
                                                            382/128
7,844,320 B2   11/2010  Shahidi
(Continued)

FOREIGN PATENT DOCUMENTS

JP    2013531525 A    8/2013
JP    2018047240 A    3/2018
(Continued)

OTHER PUBLICATIONS

PCT International Search Report and Written Opinion, PCT Application No. PCT/US20/146784, dated Apr. 21, 2020, 11 pages.
(Continued)

*Primary Examiner* — Said Broome
(74) *Attorney, Agent, or Firm* — Fenwick & West LLP (57) ABSTRACT

A mediated-reality system for surgical applications incorporates pre-operative images and real-time captured images of a surgical site into a visualization presented on a head-mounted display worn by a surgeon during a surgical procedure. The mediated-reality system tracks the surgeon's head position and generates real-time images of the surgical site from a virtual camera perspective corresponding to the surgeon's head position to mimic the natural viewpoint of the surgeon. The mediated-reality system furthermore aligns the pre-operative images with the real-time images from the virtual camera perspective and presents a mediated-reality visualization of the surgical site with the aligned pre-
(Continued)

operative three-dimensional images or a selected portion thereof overlaid on the real-time images representing the virtual camera perspective.

20 Claims, 6 Drawing Sheets

Related U.S. Application Data (60) Provisional application No. 62/796,065, filed on Jan. 23, 2019.

(51) Int. Cl.
*G06T 7/33* (2017.01)
*G06T 19/20* (2011.01)

(52) U.S. Cl.
CPC ........ *G06T 19/20* (2013.01); *A61B 2090/363* (2016.02); *A61B 2090/365* (2016.02); *A61B 2090/367* (2016.02); *A61B 2090/373* (2016.02); *A61B 2090/3983* (2016.02); *A61B 2090/3991* (2016.02); *G06T 2207/30196* (2013.01); *G06T 2207/30208* (2013.01); *G06T 2219/2004* (2013.01)

(56) References Cited

U.S. PATENT DOCUMENTS

| | | | | |
|---|---|---|---|---|
| 8,108,025 | B2 * | 1/2012 | Csavoy | A61B 90/17 |
| | | | | 600/407 |
| 8,126,224 | B2 * | 2/2012 | Zuhars | A61B 6/12 |
| | | | | 378/197 |
| 8,165,659 | B2 * | 4/2012 | Sheffer | A61B 34/20 |
| | | | | 600/407 |
| 9,314,219 | B2 * | 4/2016 | Keall | A61N 5/1049 |
| 9,532,056 | B2 * | 12/2016 | Jiang | H03M 7/40 |
| 9,972,129 | B2 * | 5/2018 | Michel | G06T 9/00 |
| 2007/0238982 | A1 * | 10/2007 | Caylor, III | A61B 5/1127 |
| | | | | 600/424 |
| 2016/0086353 | A1 * | 3/2016 | Lukac | G06T 9/00 |
| | | | | 345/419 |
| 2017/0099479 | A1 | 4/2017 | Browd et al. | |
| 2017/0323062 | A1 | 11/2017 | Djajadiningrat et al. | |

FOREIGN PATENT DOCUMENTS

| | | |
|---|---|---|
| WO | WO 2014/200017 A1 | 2/2017 |
| WO | WO 2018/097831 A1 | 5/2018 |
| WO | WO 2018/195529 A1 | 10/2018 |
| WO | WO 2019/010203 A1 | 1/2019 |

OTHER PUBLICATIONS

United States Office Action, U.S. Appl. No. 16/749,963, dated Apr. 8, 2020, 15 pages.

The Japan Patent Office, Notice of Reasons for Refusal, Japanese Patent Application No. 2021-542469, Feb. 22, 2022, 11 pages.

* cited by examiner

ALIGNING PRE-OPERATIVE SCAN IMAGES TO REAL-TIME OPERATIVE IMAGES FOR A MEDIATED-REALITY VIEW OF A SURGICAL SITE

CROSS REFERENCE TO RELATED APPLICATIONS

This application is a continuation of U.S. patent application Ser. No. 16/749,963 filed on Jan. 22, 2020, which claims the benefit of U.S. Provisional Application No. 62/796,065, filed Jan. 23, 2019, each of which are incorporated by reference in their entirety.

BACKGROUND

When performing surgeries, surgeons often rely on pre-operative three-dimensional images of the patient's anatomy such as computed tomography (CT) scan images. However, the usefulness of such pre-operative images is limited because the images cannot be easily integrated into the operative procedure. For example, because the images are captured in a pre-operative session, the relative anatomical positions captured in the pre-operative images may vary from their actual positions during the operative procedure. Furthermore, to make use of the pre-operative images during the surgery, the surgeon must divide attention between the surgical field and a display of the pre-operative images. Navigating between different layers of the pre-operative images may furthermore require significant attention that takes away from the surgeon's focus on the operation.

DETAILED DESCRIPTION

The figures and the following description relate to preferred embodiments by way of illustration only. It should be noted that from the following discussion, alternative embodiments of the structures and methods disclosed herein will be readily recognized as viable alternatives that may be employed without departing from the principles of what is claimed.

Reference will now be made in detail to several embodiments, examples of which are illustrated in the accompanying figures. It is noted that wherever practicable similar or like reference numbers may be used in the figures and may indicate similar or like functionality. The figures depict embodiments of the disclosed system (or method) for purposes of illustration only. One skilled in the art will readily recognize from the following description that alternative embodiments of the structures and methods illustrated herein may be employed without departing from the principles described herein.

A mediated-reality system for surgical applications incorporates pre-operative images and real-time captured images of a surgical site into a visualization presented on a head-mounted display worn by a surgeon during a surgical procedure. The mediated-reality system tracks the surgeon's head position and generates real-time images of the surgical site from a virtual camera perspective corresponding to the surgeon's head position to mimic the natural viewpoint of the surgeon. The mediated-reality system furthermore aligns the pre-operative images with the real-time images from the virtual camera perspective and presents a mediated-reality visualization of the surgical site with the aligned pre-operative three-dimensional images or a selected portion thereof overlaid on the real-time images representing the virtual camera perspective. The mediated-reality system thus enables the surgeon to visualize the underlying three-dimensional anatomy of a patient prior to making an incision and throughout the procedure even when anatomical features may be occluded from the surgeon's view in the real-time images. The technology furthermore beneficially provides the visualization in a manner that does not divert the surgeon's view from the surgical site, thus enhancing the surgeon's ability to perform the operation with high efficiency and precision.

In an embodiment, a patch including fiducial markers is placed on the patient's body and remains in places during the pre-operative imaging and after the patient is positioned for surgery. The fiducial markers comprise a pattern that can be recognized by the mediated-reality system in both the pre-operative images and in the real-time images captured after the patient is positioned for surgery. The mediated-reality system aligns the pre-operative images with the real-time images based on the detected positions of the fiducial markers visible in both sets of images. For example, the mediated-reality system may apply one or more transformations to the pre-operative images that causes the detected fiducial markers in the pre-operative images to align with the corresponding fiducial markers detected in the real-time images.

In another embodiment, three-dimensional images such as ultrasound or fluoroscopic images may be captured after the patient is positioned for surgery and may be utilized to predict changes in three-dimensional positions of anatomical features that occur between the pre-operative image scan and positioning the patient for surgery. The pre-operative images may then be warped to align the positioning of the anatomical features in the pre-operative image scan to the detected positions of the anatomical features seen in the three-dimensional images captured after the patient is positioned for surgery to compensate for changes that may occur.

In yet further embodiments, a combination of fiducial markers and post-positioning images may be used to align the pre-operative images to the real-time images in the mediated-reality visualization. For example, the pre-operative and post-positioning images may be compared to determine how the positions of the fiducial markers change in three-dimensional space between the images, and a transformation may be derived that transforms the pre-operative images to align the fiducial markers with their respective locations in the post-positioning images.

In a specific example embodiment, a method generates a mediated reality view of a surgical site. Pre-operative images are received that represent three-dimensional anatomy of a patient in a first position. Based on the pre-operative images, coordinates are identified in a three-dimensional pre-operative image space corresponding to locations of fiducial markers present on a patch applied to the patient. Real-time images from a camera array are received after the patient is positioned for surgery in a second position. Based on the real-time images, coordinates in a three-dimensional real-time image space are identified that correspond to locations of the fiducial markers present on the patch applied to the patient. A transformation is applied to the pre-operative images to substantially align the locations of the fiducial markers in the pre-operative images to the locations of the fiducial markers in the real-time images. The transformed pre-operative images are overlaid on the real-time images to generate the mediated reality view, and the mediated reality view is provided to a display device for display.

In another specific embodiment, a method generates a mediated reality view of a surgical site without necessarily relying on fiducial markers on a patch. In this embodiment, pre-operative images are received that represent three-dimensional anatomy of a patient in a first position. Post-positioning images captured after the patient is positioned for surgery in a second position are received. Based on the pre-operative images and the post-positioning images, a set of corresponding features visible in the pre-operative images and the post-positioning images are identified. A first transformation is applied to the pre-operative images to substantially align locations of the corresponding features in the pre-operative images to respective locations in the post-positioning images to generate initial transformed pre-operative images. The camera array captures real-time images of the patient and overlays the initial transformed pre-operative images on the real-time images to generate an initial mediated reality view which is provided to a display device for display. Further details regarding the above-described embodiments and descriptions of additional embodiments are provided below.

Figure 1:
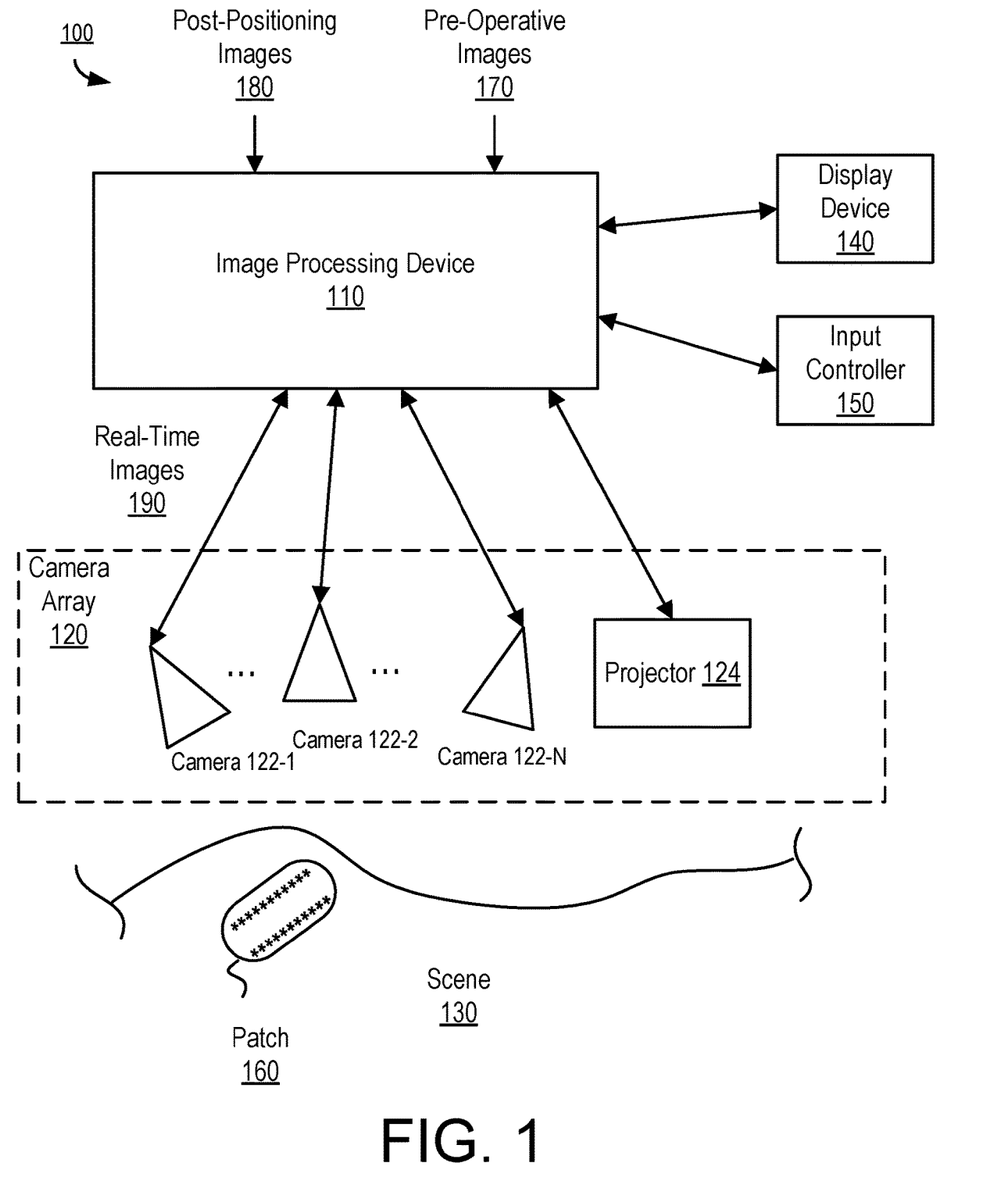
FIG. 1 is an example embodiment of an imaging system.

FIG. 1 illustrates an example embodiment of a mediated-reality system 100 comprising an image processing device 110, a camera array 120, a display device 140, and an input controller 150. In alternative embodiments, the mediated-reality system 100 may comprise additional or different components.

The camera array 120 comprises a plurality of cameras 122 (e.g., a camera 122-1, a camera 122-2, . . . , a camera 122-N) that each capture respective real-time images 190 of a scene 130. The cameras 122 may be physically arranged in a particular configuration such that their physical locations and orientations are fixed relative to each other. For example, the cameras 122 may be structurally secured by a mounting structure to mount the cameras 122 at predefined fixed locations and orientations. The cameras 122 of the camera array 120 may be positioned such that neighboring cameras may share overlapping views of the scene 130. The cameras 122 in the camera array 120 may furthermore be synchronized to capture images 190 of the scene 130 substantially simultaneously (e.g., within a threshold temporal error). The camera array 120 may furthermore comprise one or more projectors 124 that projects a structured light pattern onto the scene 130. In an embodiment, the cameras 122 may comprise light-field cameras that capture light field information of the scene 130. Here, the cameras 122 capture both the intensity of light and the directions of light rays representing the scene. The light-field images 190 thus encode depth information and enable recreation of the scene as a three-dimensional image.

The image processing device 110 receives images 190 captured by the camera array 120 and processes the images to synthesize an output image corresponding to a virtual camera perspective. Here, the output image corresponds to an approximation of an image of the scene 130 that would be captured by a camera placed at an arbitrary position and orientation corresponding to the virtual camera perspective. The image processing device 110 synthesizes the output image from a subset (e.g., one or more) of the cameras 122 in the camera array 120, but does not necessarily utilize images 190 from all of the cameras 122. For example, for a given virtual camera perspective, the image processing device 110 may select a stereoscopic pair of images 190 from two cameras 122 that are positioned and oriented to most closely match the virtual camera perspective. The image processing device 110 may furthermore detect the structured light projected onto the scene 130 by the projector to estimate depth information of the scene. The depth information may be combined with the images 190 from the cameras 122 to synthesize the output image as a three-dimensional rendering of the scene 130 as viewed from the virtual camera perspective. Alternatively, the structured light projector 124 may be omitted and the image processing device 110 may derive the three-dimensional rendering solely from the images 190 captured by the one or more cameras 122.

The virtual camera perspective may be controlled by an input controller 150 that provides a control input corresponding to the location and orientation of the virtual camera perspective. The output image corresponding to the virtual camera perspective is outputted to the display device 140 and displayed by the display device 140. The output image may be updated at a high frame rate to synthesize a video representative of the virtual camera perspective. The image processing device 110 may furthermore beneficially process received inputs from the input controller 150 and process the captured images 190 from the camera array 120 to generate output images corresponding to the virtual perspective in substantially real-time as perceived by a viewer of the display device 140 (e.g., at least as fast as the frame rate of the camera array 120).

The image processing device 110 may furthermore receive pre-operative images 170 representing a three-dimensional volume such as, for example, CT scan images, ultrasound images, or fluoroscopic images. As will be described in further detail below, the image processing device 110 may detect visual features in the pre-operative images 170 that correspond to visual features in the real-time images 190 captured by the camera array 120. The image processing device 110 may then apply one or more transformations to the pre-operative images 170 to align the detected features in the pre-operative images 170 (or portion thereof) to corresponding features detected in the real-time images 190. The image processing device 110 may apply the one or more transformations on a frame-by-frame basis such that the pre-operative images 170 are aligned with the real-time images 190 in each frame as the virtual perspective changes. The image processing device 110 overlays the pre-operative images 170 with the real-time images 190 to present a mediate-reality view that enables a surgeon to simultaneously visualize the surgical site and the underlying three-dimensional anatomy of a patient undergoing an operation.

In an embodiment, the scene 130 (e.g., a body of a surgical patient) may be prepared with a patch 160 comprising fiducial markers prior to capturing the pre-operative images 170. The image processing device 110 may identify specific features of the fiducial markers that enable it to identify correspondence between the features in the pre-operative images 170 and the real-time images 190. The image processing device 110 may apply the transformations to the pre-operative images 170 in a manner such that a pattern of the fiducial markers in the pre-operative images 170 becomes aligned with the corresponding pattern visible in the real-time images 190 from the camera array 120. For example, the pre-operative images 170 may be translated, rotated, and/or warped to align the fiducial markers with corresponding fiducial markers in the real-time images 190.

In an embodiment, the image processing device 110 optionally also receives one or more post-positioning three-dimensional images 180 captured of the scene 130 after the patient is positioned for surgery. The post-positioning images 180 may comprise, for example, ultrasound or fluoroscopic images captured once the patient is positioned for surgery. The image processing device 110 may utilize the post-positioning images 180 in determining the transformation to apply to the pre-operative images 170 to align the pre-operative images 170 to the real-time images 190. In an embodiment, the image processing device 110 may identify the fiducial markers or anatomical features in the post-positioning images 180 and apply one or more transformations to the pre-operative images 170 to align the pre-operative images 170 with the post-positioning images 180. This transformation step may beneficially correct the pre-operative images 170 for a shift in the positioning of anatomical elements to may have occurred in between capturing the pre-operative images 170 and positioning the patient for surgery.

The image processing device 110 may comprise a processor and a non-transitory computer-readable storage medium that stores instructions that when executed by the processor, carry out the functions attributed to the image processing device 110 as described herein.

The display device 140 may comprise, for example, a head-mounted display device or other display device for displaying the output images received from the image processing device 110. In an embodiment, the input controller 150 and the display device 140 are integrated into a head-mounted display device and the input controller 150 comprises a motion sensor that detects position and orientation of the head-mounted display device. The virtual perspective can then be derived to correspond to the position and orientation of the head-mounted display device such that the virtual perspective corresponds to a perspective that would be seen by a viewer wearing the head-mounted display device. Thus, in this embodiment, the head-mounted display device can provide a real-time rendering of the scene as it would be seen by an observer without the head-mounted display. Alternatively, the input controller 150 may comprise a user-controlled control device (e.g., a mouse, pointing device, handheld controller, gesture recognition controller, etc.) that enables a viewer to manually control the virtual perspective displayed by the display device.

Figure 2:
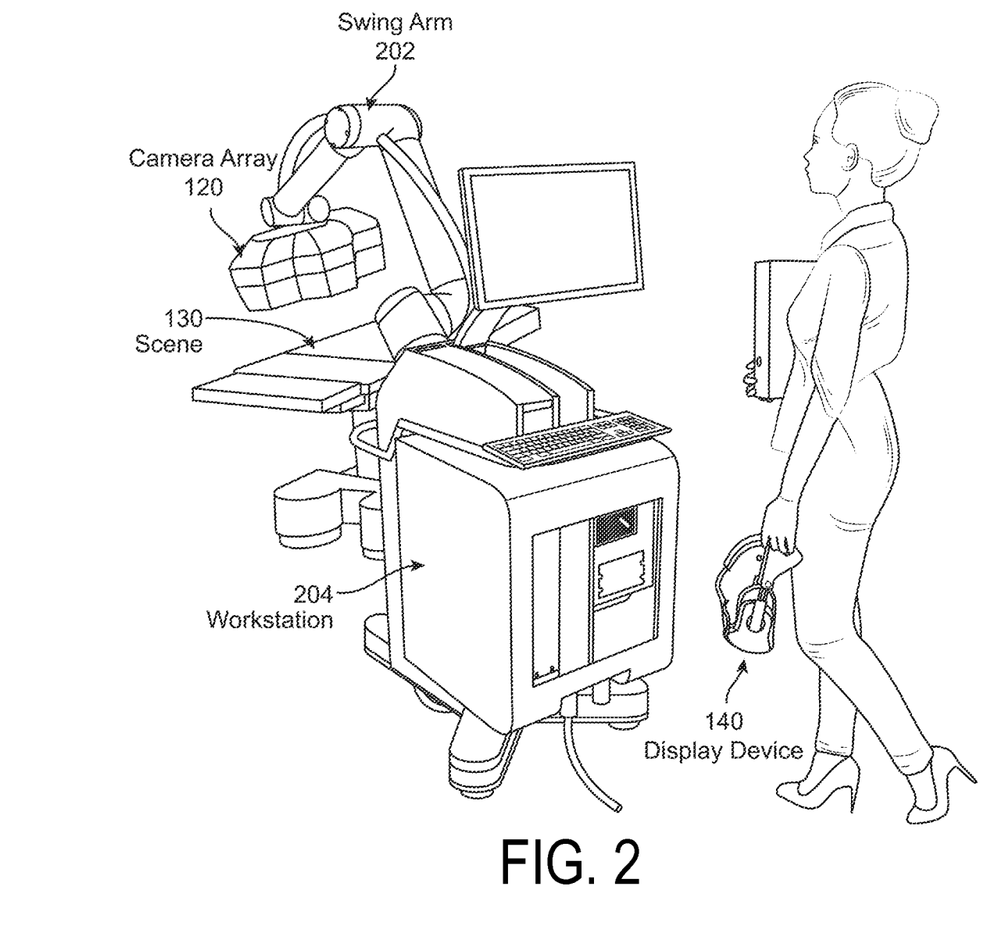
FIG. 2 is an example of a surgical environment employing the imaging system for mediated-reality assisted surgery.

FIG. 2 illustrates an example embodiment of the mediated-reality system 100 for a surgical application. Here, an embodiment of the camera array 120 is positioned over the scene 130 (in this case, a surgical site) and can be positioned via a swing arm 202 attached to a workstation 204. The swing arm 202 may be manually moved or may be robotically controlled in response to the input controller 150. The workstation 204 may include a computer to control various functions of the camera array 120 and the display device 140, and may furthermore include a secondary display that can display a user interface for performing various configuration functions, or may mirror the display on the display device 140. The image processing device 120 and the input controller 150 may each be integrated in the workstation 204, the display device 140, or a combination thereof.

Figure 3A:
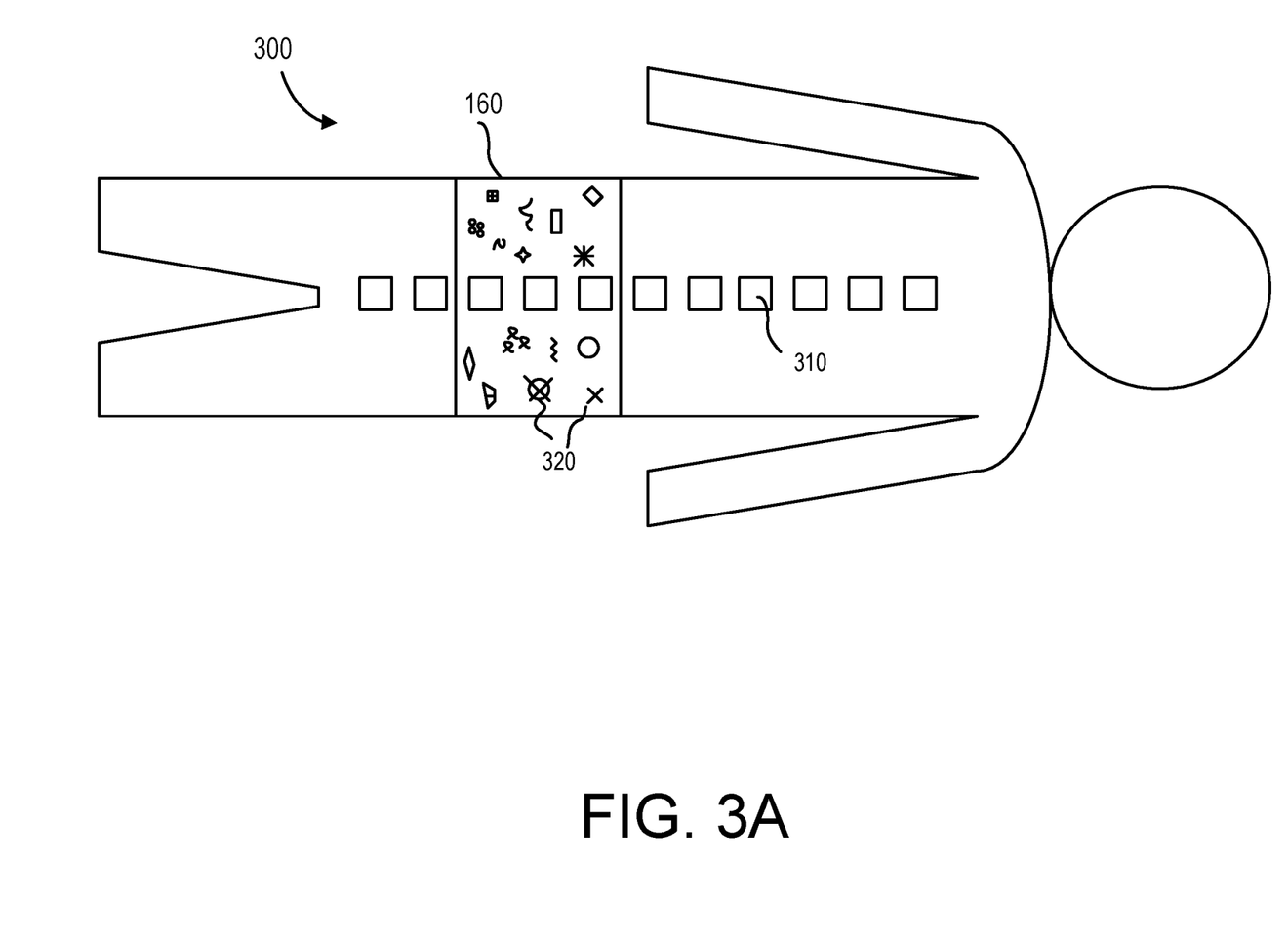
FIG. 3A is a top plan view of an embodiment of a body patch with fiducial markers for aligning real-time operative images to pre-operative scan images.

FIG. 3A illustrates an example embodiment of a patch 160 applied to a patient 300 that may be utilized to align pre-operative images 170 with real-time captured images 190 in a mediated-reality system 100. In an embodiment, the patch 160 comprises a thin flexible adhesive patch that can be applied to a patient's skin and conform to the contours of the patient's body. The patch 160 may be positioned proximate to an anatomical structure of interest for the relevant surgical procedure (e.g., vertebrates 310). The patch 160 may include a pattern of three-dimensional fiducial markers 320 that can be uniquely identified by the image processing device 110 in both the pre-operative images 170 and the real-time images 190 even when viewed from different perspectives and under different lighting conditions. For example, the fiducial markers 320 may each comprise one or more raised surfaces forming a recognizable three-dimensional geometry. In an embodiment, each marker may be unique within a particular region of the patch 160. In an embodiment, a patch 160 comprises a grid (which may be uniform or non-uniform) of fiducial markers each having a unique three-dimensional geometry and which can each be uniquely recognized in the pre-operative images 170 and the real-time images 190 and which can each be correlated to a particular position on the human body. The fiducial markers 320 may each comprise materials of different densities that can be distinguished by ultrasound or radio opaque images.

In an embodiment, the patch 160 may be partitioned into sections separated by perforated boundaries. The perforations enable one or more sections of the patch 160 to be easily removed from the patient without removing the entire patch 160. For example, in one use case, the surgeon may remove a section of the patch over the desired incision location after the patient is positioned for surgery and the image processing device 110 performs an initial alignment computation. The remaining sections of the patch 160 that are not directly over the incision location may remain in place. The image processing system 110 may continue to detect the fiducial markers 320 on the remaining portion of the patch 160 throughout the operation to update the alignment.

Figure 3B:
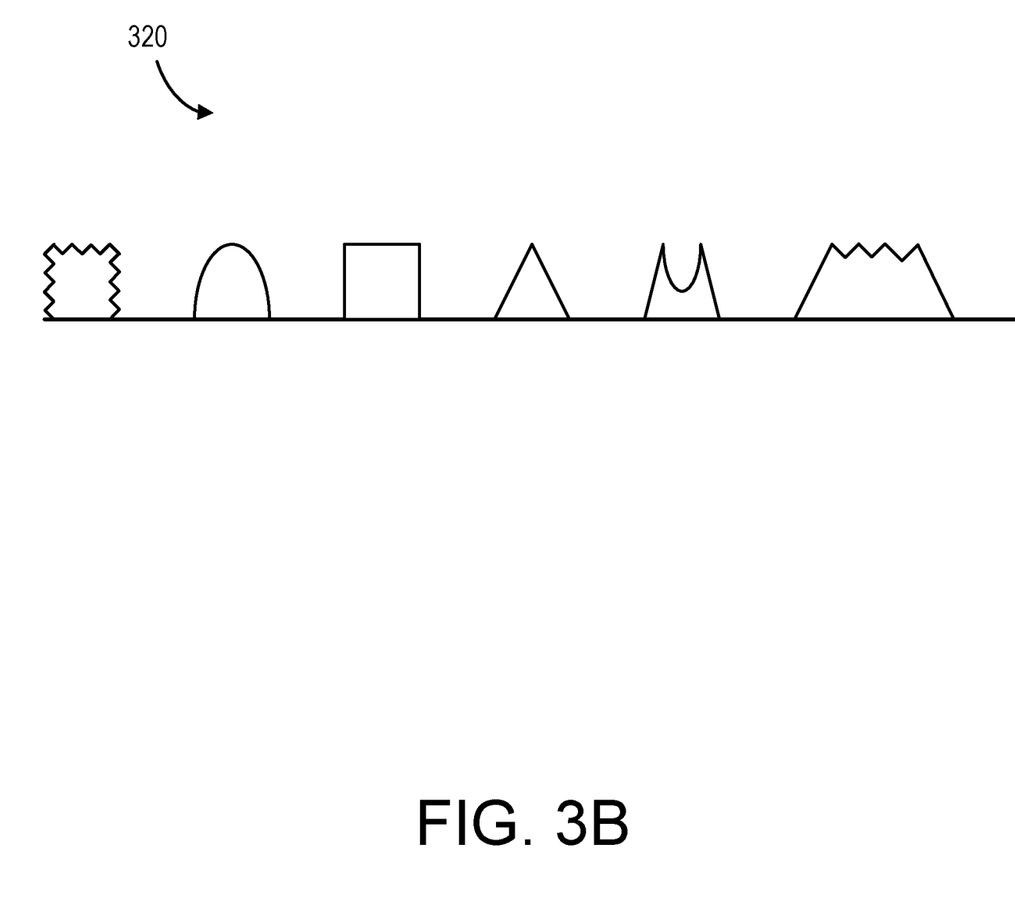
FIG. 3B is a cross-sectional view of an embodiment of a body patch with fiducial markers for aligning real-time operative images to pre-operative scan images.

FIG. 3B illustrates example cross-sectional views of example fiducial markers 320 that may be integrated with a patch 160. As illustrated, the fiducial markers 320 have varying three-dimensional structures and may include varying densities that enables the markers 320 to be distinguished from each other in the real-time images 190, pre-operative images 170, and post-positioning images 180.

Figure 4:
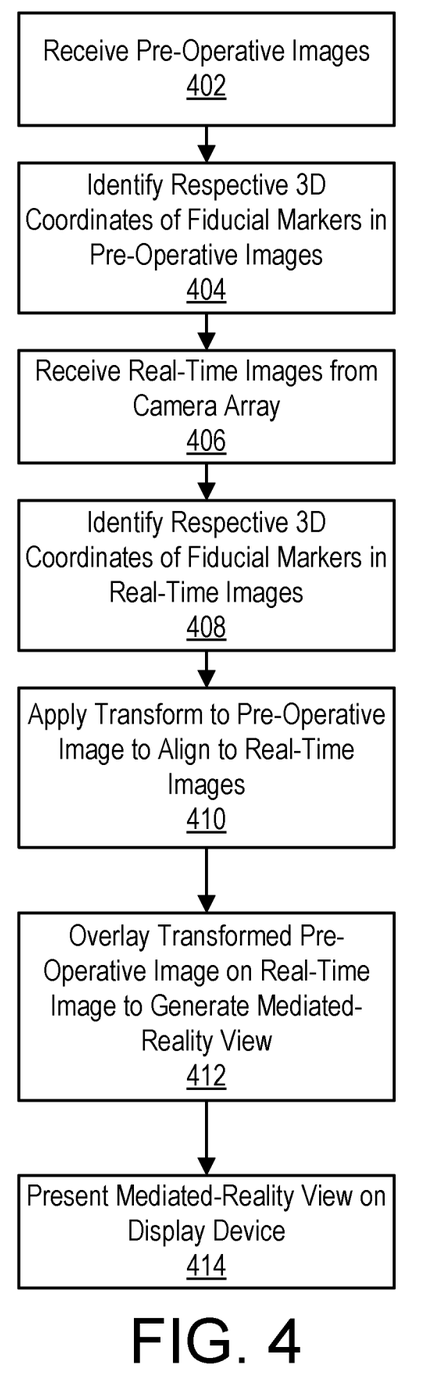
FIG. 4 is a flowchart illustrating an embodiment of a process for generating a mediated-reality view of a surgical site based on pre-operative images.

FIG. 4 illustrates an example embodiment of a process for generating a mediated-reality visualization of a surgical site with pre-operative images 170 aligned and overlaid on real-time images 190. The image processing device 110 receives 402 the pre-operative images 170. The image processing device 110 identifies 404 respective three-dimensional coordinates corresponding to the locations of the fiducial markers in the pre-operative images 170. For example, the image processing device 110 detects the fiducial markers in the pre-operative images 170 and maps the fiducial markers to a first set of three-dimensional coordinates representing a location of the human body in the pre-operative image space. For example, the image processing device 110 may obtain a predefined mapping between uniquely recognizable structures of the fiducial markers and their corresponding locations on the patch 160. The image processing device 110 receives 406 real-time images 190 of a scene captured by the camera array 120. The image processing device 110 identifies 408 respective three-dimensional coordinates corresponding to locations of the fiducial markers in the real-time images 190. For example, the image processing device 110 detects the fiducial markers in the real-time images 190 and maps each fiducial marker to a second set of three-dimensional coordinates representing a location on the human body in the real-time image space. The image processing device 110 then applies 410 one or more transformations to the pre-operative images 170 that substantially aligns the pattern of fiducial markers in the pre-operative images 170 to the pattern in the real-time images 190. For example, in one embodiment, the image processing device 110 performs an optimization algorithm to identify a transformation that minimizes a distance between transformed coordinates of the pattern in the pre-operative images 170 with corresponding coordinates of the pattern in the real-time images 190. The image processing device 110 overlays 412 the transformed pre-operative images on the real-time images to generate the mediated-reality view. The mediated-reality view is then provided 414 to the display device 140 for display.

Figure 5:
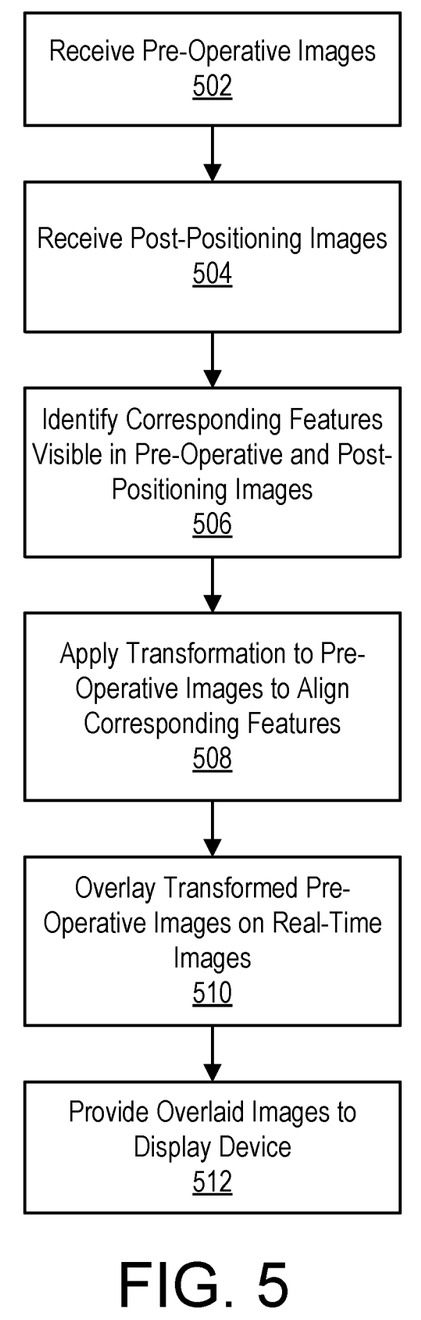
FIG. 5 illustrates an embodiment of a process for aligning pre-operative images captured prior to a patient being positioned for surgery to post-positioning images captured after a patient is positioned for surgery.

FIG. 5 illustrates an embodiment of a process for aligning pre-operative images 170 captured prior to a patient being positioned for surgery to post-positioning images 180 captured after a patient is positioned for surgery. An image processing device 110 receives 502 the pre-operative images 170. The pre-operative images may comprise, for example, CT scan images. The image processing device 110 receives 504 the post-positioning images 180 captured after a patient is positioned for surgery. The post-positioning images 180 may comprise, for example, ultrasound or fluoroscopic images. The image processing device 110 identifies 506 a set of corresponding features (e.g., anatomical features or fiducial markers on a patch) visible in both the pre-operative images 170 and the post-positioning images 180. The image processing device 110 then applies 508 a transformation to the pre-operative images 170 that substantially aligns the locations of the corresponding features in the pre-operative images to the locations in the post-positioning images 180. For example, the image processing device 110 may apply a translation, rotation, warping, or combination thereof that minimizes a distance between transformed coordinates of the features in the pre-operative images 170 with coordinates of corresponding features in the post-positioning images 180. The transformation beneficially compensates for shifts in the position of anatomical features that may occur between capturing the pre-operative images 170 and positioning the patient for surgery. The transformed pre-operative images 170 may then be overlaid 510 on real-time images 190 captured by the camera array 120 and provided 512 to a display device 140 for display as a mediated-reality view of the surgical site.

In yet further embodiments, a transformation may be applied to pre-operative images 170 based on both post-positioning images 180 and fiducial markers detected in the real-time images 190. For example, in one embodiment, a first transformation is applied to pre-operative images 170 in accordance with the process of FIG. 5 to obtain an initial transformation. A second transformation is then applied according to the process of FIG. 4 to refine the alignment in each image frame based on the pattern of fiducial markers detected in the pre-operative images 170 and the real-time images 190.

Upon reading this disclosure, those of skill in the art will appreciate still additional alternative structural and functional designs for the disclosed embodiments as disclosed from the principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and system disclosed herein without departing from the scope of the described embodiments.

The invention claimed is:

1. A method for generating a mediated reality view of a surgical site comprising:
   receiving pre-operative images representing three-dimensional anatomy of a patient in a first position;
   receiving post-positioning images captured after the patient is positioned for surgery in a second position;
   identifying, based on the pre-operative images and the post-positioning images, a set of corresponding features visible in the pre-operative images and the post-positioning images;
   applying a first transformation to the pre-operative images to substantially align locations of the corresponding features in the pre-operative images to respective locations in the post-positioning images to generate initial transformed pre-operative images;
   capturing, by a camera array, real-time images of the patient;
   overlaying the initial transformed pre-operative images on the real-time images to generate an initial mediated reality view; and
   providing the initial mediated reality view to a display device for display.

2. The method of claim 1, wherein the features comprise anatomical features of a body of the patient.

3. The method of claim 1, wherein the features comprise fiducial markers on a patch applied to a body of the patient.

4. The method of claim 3, wherein the patch comprises a flexible adhesive patch positioned proximate to an anatomical structure of interest.

5. The method of claim 3, wherein the fiducial markers comprise three-dimensional structures including one or more raised surfaces, and wherein each of the fiducial markers has a unique geometry relative to other fiducial markers on the patch.

6. The method of claim 3, wherein the fiducial markers are arranged in a grid on the patch.

7. The method of claim 3, wherein the fiducial markers comprise materials of different densities that are distinguishable in the real-time images.

8. The method of claim 3, wherein the patch comprises perforated boundaries for tearing the patch into sections.

9. The method of claim 1, further comprising:
   identifying, based on the pre-operative images, coordinates in a three-dimensional pre-operative image space corresponding to locations of fiducial markers present on a patch applied to the patient;
   identifying, based on the real-time images, coordinates in a three-dimensional real-time image space corresponding to locations of the fiducial markers present on the patch applied to the patient;
   applying a second transformation to refine an alignment of the locations of the fiducial markers in the pre-operative images to the locations of the fiducial markers in the real-time images to generated refined pre-operative images;

overlaying the refined pre-operative images on the real-time images to generate a refined mediated reality view; and providing the refined mediated reality view to the display device for display.

10. A non-transitory computer-readable storage medium storing instructions for generating a mediated reality view of a surgical site, the instructions when executed by a processor of a mediated reality system, cause the mediated reality system to:

receive pre-operative images representing three-dimensional anatomy of a patient in a first position;

receive post-positioning images captured after the patient is positioned for surgery in a second position;

identify, based on the pre-operative images and the post-positioning images, a set of corresponding features visible in the pre-operative images and the post-positioning images;

apply a first transformation to the pre-operative images to substantially align locations of the corresponding features in the pre-operative images to respective locations in the post-positioning images to generate initial transformed pre-operative images;

capture, by a camera array, real-time images of the patient;

overlay the initial transformed pre-operative images on the real-time images to generate an initial mediated reality view; and provide the initial mediated reality view to a display device for display.

11. The non-transitory computer-readable storage medium of claim 10, wherein the features comprise anatomical features of a body of the patient.

12. The non-transitory computer-readable storage medium of claim 10, wherein the features comprise fiducial markers on a patch applied to a body of the patient.

13. The non-transitory computer-readable storage medium of claim 12, wherein the patch comprises a flexible adhesive patch positioned proximate to an anatomical structure of interest.

14. The non-transitory computer-readable storage medium of claim 12, wherein the fiducial markers comprise three-dimensional structures including one or more raised surfaces, and wherein each of the fiducial markers has a unique geometry relative to other fiducial markers on the patch.

15. The non-transitory computer-readable storage medium of claim 12, wherein the fiducial markers are arranged in a grid on the patch.

16. The non-transitory computer-readable storage medium of claim 12, wherein the fiducial markers comprise materials of different densities that are distinguishable in the real-time images.

17. The non-transitory computer-readable storage medium of claim 12, wherein the patch comprises perforated boundaries for tearing the patch into sections.

18. The non-transitory computer-readable storage medium of claim 10, further comprising stored instructions that when executed cause the mediated reality system to:

identify, based on the pre-operative images, coordinates in a three-dimensional pre-operative image space corresponding to locations of fiducial markers present on a patch applied to the patient;

identify, based on the real-time images, coordinates in a three-dimensional real-time image space corresponding to locations of the fiducial markers present on the patch applied to the patient;

apply a second transformation to refine an alignment of the locations of the fiducial markers in the pre-operative images to the locations of the fiducial markers in the real-time images to generated refined pre-operative images;

overlay the refined pre-operative images on the real-time images to generate a refined mediated reality view; and provide the refined mediated reality view to the display device for display.

19. A mediated reality system comprising:

a camera array;

a display device;

a processor; and a non-transitory computer-readable storage medium storing instructions for generating a mediated reality view of a surgical site, the instructions when executed by a processor of the mediated reality system, cause the mediated reality system to:

receive pre-operative images representing three-dimensional anatomy of a patient in a first position;

receive post-positioning images captured after the patient is positioned for surgery in a second position;

identify, based on the pre-operative images and the post-positioning images, a set of corresponding features visible in the pre-operative images and the post-positioning images;

apply a first transformation to the pre-operative images to substantially align locations of the corresponding features in the pre-operative images to respective locations in the post-positioning images to generate initial transformed pre-operative images;

capture, by the camera array, real-time images of the patient;

overlay the initial transformed pre-operative images on the real-time images to generate an initial mediated reality view; and provide the initial mediated reality view to the display device for display.

20. The mediated reality system of claim 19, wherein the display device comprises a head-mounted display device.

* * * * *